United States Patent [19]
Throne et al.

[11] Patent Number: 5,000,189
[45] Date of Patent: Mar. 19, 1991

[54] METHOD AND SYSTEM FOR MONITORING ELECTROCARDIOGRAPHIC SIGNALS AND DETECTING A PATHOLOGICAL CARDIAC ARRHYTHMIA SUCH AS VENTRICULAR TACHYCARDIA

[75] Inventors: Robert D. Throne; Janice M. Jenkins; Lorenzo A. DiCarlo, all of Ann Arbor, Mich.

[73] Assignee: Regents of the University of Michigan, Ann Arbor, Mich.

[21] Appl. No.: 437,079

[22] Filed: Nov. 15, 1989

[51] Int. Cl.$^5$ .............................................. A61B 5/04
[52] U.S. Cl. ..................................... 128/702; 128/705
[58] Field of Search ................. 128/695, 696, 700–708

[56] References Cited
U.S. PATENT DOCUMENTS

| | | | |
|---|---|---|---|
| 4,259,966 | 4/1981 | Cannon et al. | 128/706 |
| 4,583,553 | 4/1986 | Shah et al. | 128/708 |
| 4,704,681 | 11/1987 | Shimizu et al. | 128/706 |
| 4,893,632 | 1/1990 | Armington | 128/708 |

Primary Examiner—Francis Jaworski
Assistant Examiner—George Manuel
Attorney, Agent, or Firm—Brooks & Kushman

[57] ABSTRACT

A method and system are provided for monitoring electrocardiographic signals and detecting a pathological cardiac arrhythmia, such as ventricular tachycardia wherein the zero crossings of the first derivative of a reference template (i.e. reference waveform) are utilized to separate or partition both the template and each subsequent electrocardiographic signal being monitored into first and second sets of identifiable partitions. Each zero crossing is a boundary between adjacent partitions. Initially, the reference template is generated by acquiring a first set of wavefrom data representing a known good electrocardiographic signal. Identifiable partitions of the first set of data are then matched with corresponding identifiable partitions of the second set of data to obtain a performance measure signal. In one embodiment, the area beneath the derivative in each partition of the analyzed waveform is computed and compared (i.e. matched) to the corresponding area of the template. Preferably, a plurality of electrocardiographic signals are analyzed by utilizing the template and a plurality of performance measure signals are obtained. Finally, a therapy signal is provided as a function of the plurality of performance measure signals in the event of a pathologica cardiac arrhythmia, such as ventricular tachycardia.

12 Claims, 5 Drawing Sheets

METHOD AND SYSTEM FOR MONITORING ELECTROCARDIOGRAPHIC SIGNALS AND DETECTING A PATHOLOGICAL CARDIAC ARRHYTHMIA SUCH AS VENTRICULAR TACHYCARDIA

TECHNICAL FIELD

This invention relates to a method and system for monitoring electrocardiographic signals and detecting a pathological cardiac arrhythmia, such as ventricular tachycardia, based on the morphology of the electrocardiographic signals.

BACKGROUND ART

Electrical management of intractable ventricular tachycardia via implantable antitachycardia devices has become a major form of therapy. There are many proposed methods for differentiating sinus rhythm from ventricular tachycardia (VT). Most early methods were based primarily on timing information which could be implemented in the existing hardware available in antitachycardia devices. Besides sustained high rate, simple measures derived from rate have been examined for more precise detection of ventricular tachycardia. These include the maximal rate of sinus tachycardia compared to the onset of VT, changes in rate at the onset of VT, and rate stability during VT.

Among the methods most widely used for detection of VT in single chamber antitachycardia devices are rate, rate stability, and sudden onset. These methods use some modern digital circuitry but are based on hardware trigger detection and ignore the information content of the intraventricular signal itself. An example of these methods is disclosed in U.S. Pat No. 3,857,398. U.S. Pat. No. 4,393,877 attempts to determine heart rate and includes a differentiator and a zero crossing detector connected in parallel to receive the ECG signal and other circuitry to develop a single count for each PQRST waveform and avoid overcounting.

Along with rate, morphology differences between ventricular electrograms during sinus rhythm and ventricular tachycardia are being investigated for more accurate discrimination. One commercially available device for treatment of VT uses rate alone or both rate and a probability density function (PDF) as an attempt to discriminate sinus rhythm from ventricular fibrillation. It has been less reliable in distinguishing VT from sinus rhythm. Such a device is disclosed in U.S. Pat. No. 4,184,493. Other U.S. patents which disclose various detection devices include U.S. Pat. Nos. 3,577,983; 3,616,791; 3,821,948; 3,861,387; 3,878,833; 3,902,479; 3,940,692; 4,170,992; 4,296,755 and 4,523,595.

Recently, investigators have proposed a variety of schemes for detection of VT based on analysis of the ventricular electrocardiogram. Amplitude distribution analysis, a software algorithm similar to PDF, has also been tested with limited success. Some success has been reported using a gradient pattern detection (GPD) method, described in a paper by D. W. Davies, R. J. Wainwright, M. A. Tooley, D. Lloyd, A. W. Nathan, R. A. J. Spurrell, and A. J. Camm, entitled "Detection of Pathological Tachycardia by Analysis of Electrogram Morphology", PACE, Vol. 9, pp. 200-208, Mar.-Apr. 1986, which proposes discrimination of ventricular electrograms during sinus rhythm from those during VT by using the order in which the first derivative of the ventricular depolarization crosses predetermined thresholds. Such crossings are directly dependent on the amplitude of the waveforms under analysis. Hence fluctuations in amplitude may cause ventricular depolarization with identical morphology to be classified differently. There is no performance measure in the GPD algorithm to determine how closely a waveform matches the template. Thus there appears to be no general means for setting thresholds to discriminate sinus rhythm depolarization from those during ventricular tachycardia using the GPD algorithm.

Another technique proposed for detecting VT combines bandpass filtering, rectifying, amplitude scaling, and signal integration over a 5-second moving time window. A feature extraction algorithm utilizing the product of the peak amplitude difference (maximum-minimum) and duration (time between maximum and minimum) has been presented, but has been tested on only four patients.

In other studies, the use of amplitude, dV/dt, and the $-3$ dB point of the frequency domain power spectrum have not been consistently successful in discriminating sinus rhythm from VT.

Another method, the area of difference method, demonstrated successful results in 10 patients. However, the results can be adversely affected by fluctuation in electrogram amplitude and baseline changes.

Recently, the reliability and robustness of correlation waveform analysis (CWA) has been shown for differentiating sinus rhythm from VT. CWA has the advantage of being independent of amplitude and baseline fluctuations, and produces an index of merit reflecting morphological changes only.

Correlation waveform analysis employs the correlation coefficient, $\rho$, a performance measure for analysis of similarity between a template and waveform under analysis. The correlation coefficient is independent of amplitude fluctuations, baseline changes, and produces an output between -1 and 1. Mathematically, the correction coefficient is defined as, $$\rho = \frac{\sum_{i=1}^{i=N}(t_i - t)(s_i - s)}{\sqrt{\sum_{k=1}^{k=N}(t_k - t)^2}\sqrt{\sum_{k=1}^{k=N}(s_k - s)^2}}$$

The correlation coefficient is equivalent to the following squared-error norm:

$$\rho = 1 - \frac{1}{2}\sum_{i=1}^{i=N}\left(\frac{t_i - t}{\sqrt{\sum_{k=1}^{k=N}(t_k - t)^2}} - \frac{s_i - s}{\sqrt{\sum_{k=1}^{k=N}(s_k - s)^2}}\right)^2$$

To avoid computing the square root, the performance measure is:

$$p = sign(\rho)\rho^2$$

where:
  $t_i =$ the template points.
  $s_i =$ the signal points to be processed.
  $t =$ the template average.
  $s =$ the signal average.

$s_i$ = the first derivative of the signal points.
$\phi$ = the value of the performance measure.

The correlation coefficient has been shown to produce a reliable measure for recognition of waveform changes.

SUMMARY OF THE INVENTION

An advantage of the present invention is to provide a method and system for producing results similar to CWA but which are computationally simpler and less demanding of power.

Another advantage of the present invention is to provide a comparatively simple method and system for monitoring electrocardiographic signals and detecting a pathological cardiac arrhythmia based solely on changes in the ventricular electrogram morphology and which method and system are independent of fluctuations of the baseline between ventricular electrograms and changes in electrogram amplitudes and which produce a bounded error measure.

The computational requirements of the method and system range from one-eighth to one-twelfth those of CWA.

In obtaining the above advantages and other advantages of the present invention, a method for monitoring electrocardiographic signals and detecting a pathological cardiac arrhythmia such as ventricular tachycardia in a subject, such as a human, is provided. The method includes the step of generating a reference template which includes the step of acquiring a first set of waveform data representing a known good electrocardiographic signal. The step of generating also includes the step of processing the first set of waveform data to obtain the reference template and to separate the reference template into a first set of identifiable partitions having a boundary between adjacent partitions. The step of processing includes the step of substantially determining the first derivative of the reference template. The first derivative is utilized to obtain boundary data representing the location of the boundary. The first set of identifiable partitions and the boundary data is then stored. The method also includes the step of acquiring a second set of waveform data representing a 2-D waveform of an electrocardiographic signal being monitored. The first set of identifiable partitions and the boundary data are retrieved and the second set of waveform data is processed with the boundary data to separate the monitored waveform into a second set of identifiable partitions. The first set of identifiable partitions is then matched with the corresponding identifiable partitions of the second set to obtain a performance measure signal. A plurality of electrocardiographic signals are processed in this fashion and a corresponding plurality of performance measure signals are obtained. Finally, a therapy signal is provided based on the plurality of performance measure signals which therapy signal is provided in the event of a pathological cardiac arrhythmia.

Further in obtaining the above advantages and other advantages of the present invention, a system for carrying out the above method is also provided. Preferably, each boundary between adjacent partitions represents a change between a positive derivative and a negative derivative for adjacent time intervals.

Also, preferably, the method includes the step of comparing the rate of monitored electrocardiographic signals with a predetermined rate and only requires the second set of waveform data to be processed when the measured rate exceeds the predetermined rate.

In one embodiment, the identifiable partitions include area data and, in a second embodiment, the identifiable partitions include linear data.

The objects, features and advantages of the present invention are readily apparent from the following detailed description of the best mode for carrying out the invention when taken in connection with the accompanying drawings.

BEST MODE FOR CARRYING OUT THE INVENTION

In general, the method and system of the present invention provides a rapid and reliable way of detecting a pathological cardiac arrhythmia, such as ventricular tachycardia, by utilizing the shape or morphology of an electrocardiographic signal, such as a ventricular signal. The method and system are independent of amplitude and baseline fluctuations, are computationally efficient and produce a bounded error measure for use in therapy by an implantable antitachycardia device, such as pacemaker.

Figure 1:
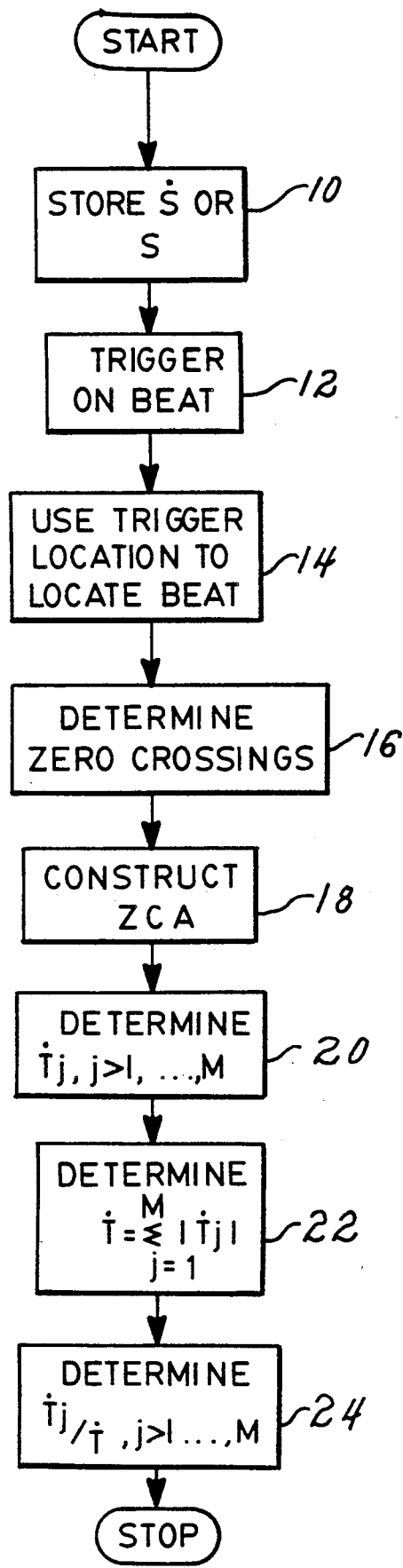
FIG. 1 is a block diagram flow chart of a template generating process of the present invention.
Figure 3:
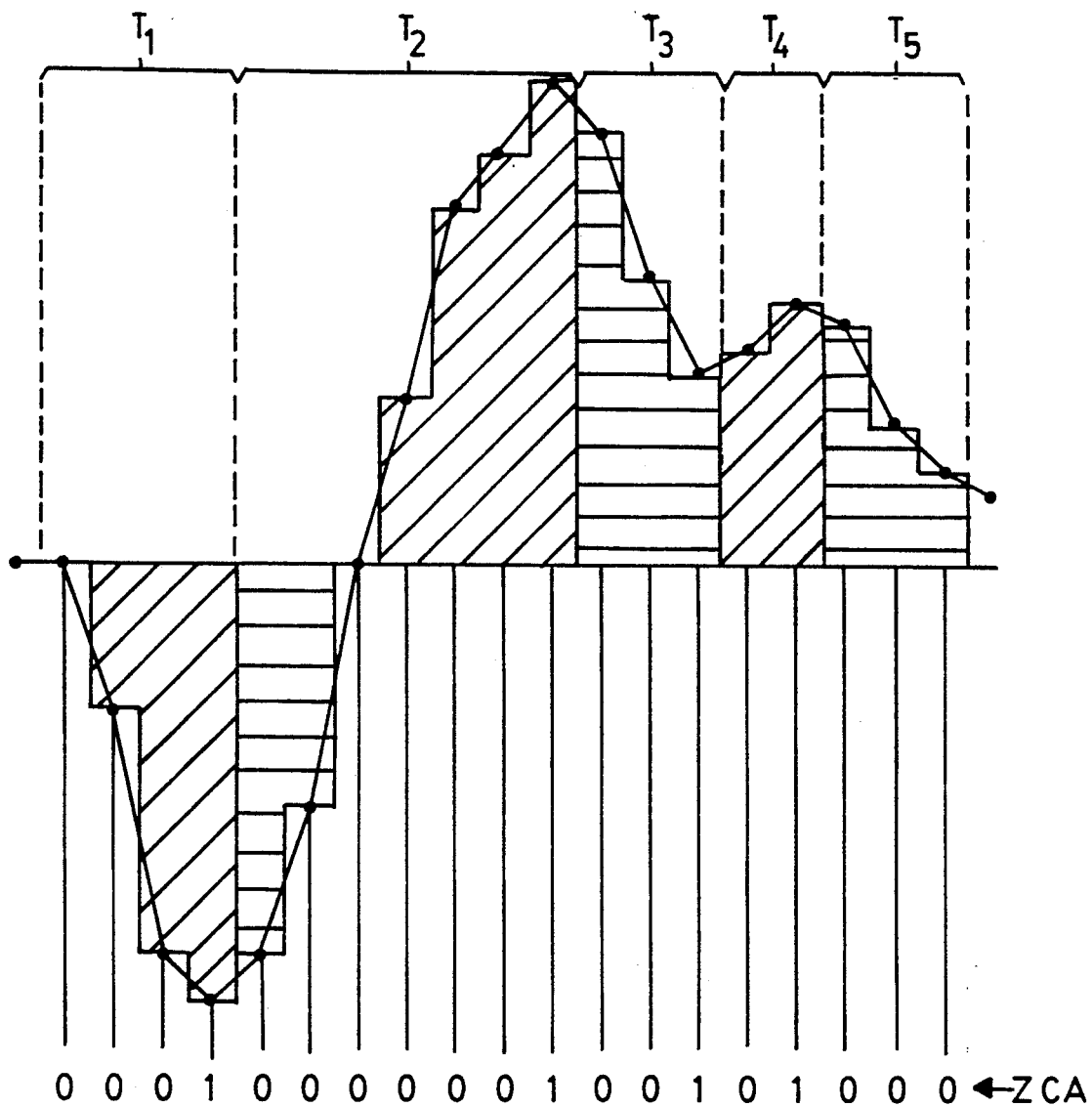
FIG. 3 is a graph of a first set of waveform data representing a known good electrocardiographic signal, the waveform data representing a 2-D reference waveform or normal template.
Figure 4:
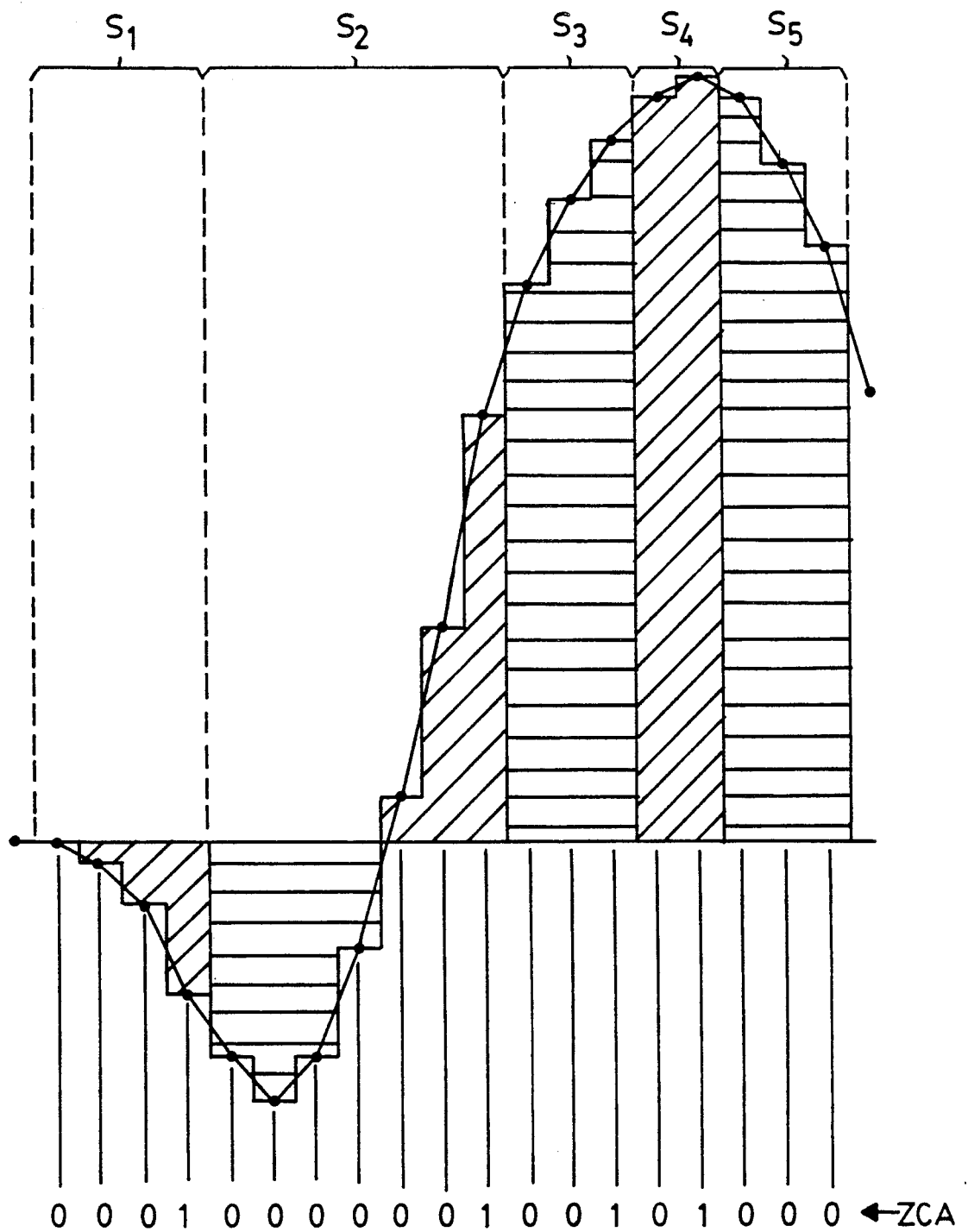
FIG. 4 is a graph of a second set of waveform data representing a 2-D waveform of an electrocardiographic signal being monitored.

Initially, a reference template or waveform, such as shown in FIG. 3, is generated by the steps illustrated in FIG. 1. In one embodiment, ventricular or electrocardiographic signals are acquired from distal bipolar endocardial electrodes positioned in the right ventricular apex of the heart of the subject, which is typically a human. The ventricular signals are amplified and filtered with the filter having settings of either 0.5 or 1 to 500 Hz. The ventricular signal is digitized with an analog-to-digital system at a sampling rate, for example, 1,000 Hz.

Figure 5:
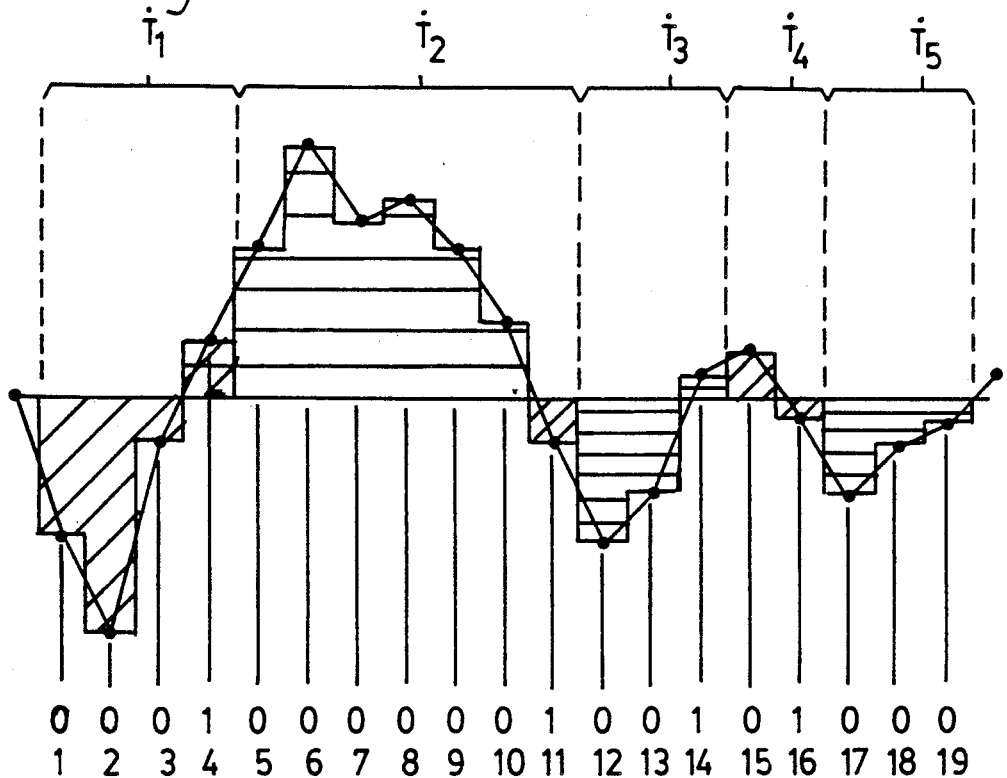
FIG. 5 is a graph of the derivative of a waveform for construction of the template derivative areas $T_k$ and the Zero Crossing Array (ZCA) for use in the method of the present invention.

As indicated at block 10 of FIG. 1, either the ventricular signal is stored or the derivative of the ventricular signal as indicated in FIG. 5, is obtained and stored in memory of a programmed computer, such as a microcomputer which may form part of the implantable device.

A software trigger, as illustrated at block 12, is utilized for detection of waveforms. It should be understood, however, that other types of triggers besides software triggers may be utilized. It is also to be understood that the other steps of the method may be utilized in software, hardware (either digital or analogue or a combination of both) or firmware or a combination of any two or three of software, hardware and firmware.

In block 14 the trigger location is utilized to locate the beat or the electrocardiographic signal.

At block 16 and as indicated in FIG. 5, the zero crossings of the derivative of the reference template are determined.

At block 18 a zero crossing array (ZCA) is constructed, as indicated at the lower edge of FIG. 5.

At block 20, the template derivative areas are computed by summing values of the derivative of the template for each point which has a "zero" in the ZCA. When a "one" occurs in the ZCA, the current derivative value is included in the area, but a new summation begins for the subsequent area.

As indicated at block 22, each template derivative area is then added together to obtain a total template derivative area.

Finally, at block 24, the ratio of each template derivative area to the total template derivative area is obtained for each template derivative area.

Figure 2:
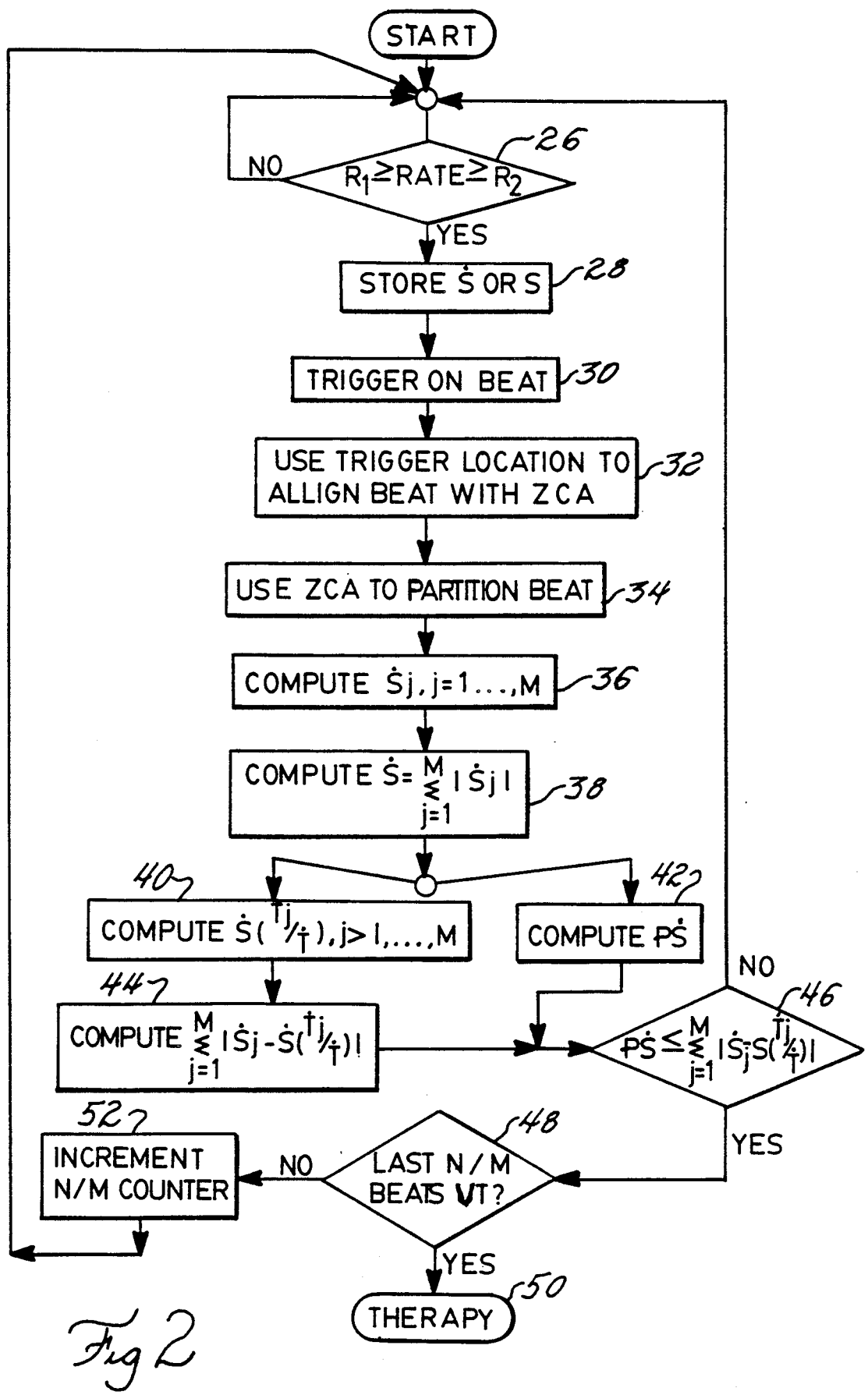
FIG. 2 is a block diagram flow chart of one embodiment of the method of the present invention.

Referring now to FIG. 2, a derivative area method (DAM) or algorithm of the present invention is described.

At block 26, the rate of monitored intracardiac signals is determined and compared with a predetermined maximum rate, $R_1$ and a predetermined threshold rate, $R_2$. If the rate is less than $R_1$ and the predetermined threshold rate is exceeded, a second set of waveform data, or its derivative, which represents a 2-D waveform of the electrocardiographic signal being monitored, is stored at block 28. If the rate is greater than $R_1$ then the algorithm is bypassed and therapy is immediately entered.

Again, a software trigger is used for detection of the waveform, as indicated at block 30. Many possible methods can be used for alignment of templates with each waveform. A template may be initially aligned, using a maximum departure from the baseline method and the appropriate performance measure is computed as is indicated hereinbelow. Alternatively, a best fit algorithm may be used to align the template with the waveforms under analysis.

At block 34, zero crossings of the derivative of the normal template is used to partition the waveform under analysis.

At block 36, the area beneath the derivative in each partition of the analyzed waveform is computed.

At block 38, the sum of the absolute values of the partitioned areas beneath the derivative of the analyzed waveform is computed.

At block 40, the area computed at block 38 is scaled by the ratio determined at block 24 of the template generation algorithm. At block 44, the area beneath the derivative in each partition of each of the analyzed waveforms is compared or matched to the corresponding area of the normal template.

At the same time the computation of block 40 is being performed, the computation of block 42 may also be performed. At block 42, a performance measure is given as follows:

$$\rho = 1 - \sum_{k=1}^{k=M} \left| \frac{T_k}{\sum_{j=1}^{j=M} |T_j|} - \frac{S_k}{\sum_{j=1}^{j=M} |S_j|} \right|$$

performance measure of Equation 1 is multiplied by the total area computed at block 38. At block 46, the result of block 42 is compared with the result of block 44 and if the result of block 42 is larger, then block 26 is reentered. If larger, the monitored electrocardiographic signal does not indicate a pathological cardiac arrhythmia.

However, if the result of block 42 is smaller than the result of block 44, at block 48 it is determined whether the last N of M monitored electrocardiographic signals satisfy the relationship of block 46. If this condition exists, block 50 is entered, which indicates that some type of cardiac therapy, such as electroshock therapy, should be entered.

If the result of block 48 is "no", a counter is incremented at block 52 and subsequent electrocardiographic signals are again monitored.

The DAM algorithm of FIG. 2 is capable of discriminating VT from sinus rhythm, using either the maximum departure, or best fit trigger location. Results from using the DAM algorithm of FIG. 2 are similar to those of CWA. While DAM does not have a predefined number of multiplications, the number of multiplications is believed to be a relatively small percentage (i.e. 10%) of that required by CWA.

The present invention provides a computationally efficient method and system to achieve real time cycle-to-cycle analysis of ventricular signals, both during sinus rhythm and ventricular tachycardia. At the same time the present method exhibits discriminatory power equivalent to CWA. The present invention provides an amplitude independent technique to analyze ventricular signals with a computational cost consistent with the power limitations of modern antitachycardia devices, such as a pacemaker.

Another possible implementation of the method and system of the invention is described below. This version uses the fact that, in continuous time, the integral of the derivative is just the difference between the original and final points.

Notation $t_i$ = the $i^{th}$ template point.
$s_i$ = the $i^{th}$ signal or waveform point (under analysis).
$t_i$ = the first derivative of the $i^{th}$ template point.
$s$ = the first derivative of the $i^{th}$ signal point.
$T_k$ = the sum of the $T_i$ in the $K^{th}$ partition.
$S_k$ = the sum of the $s_i$ in the $k^{th}$ partition.

Figure 6:
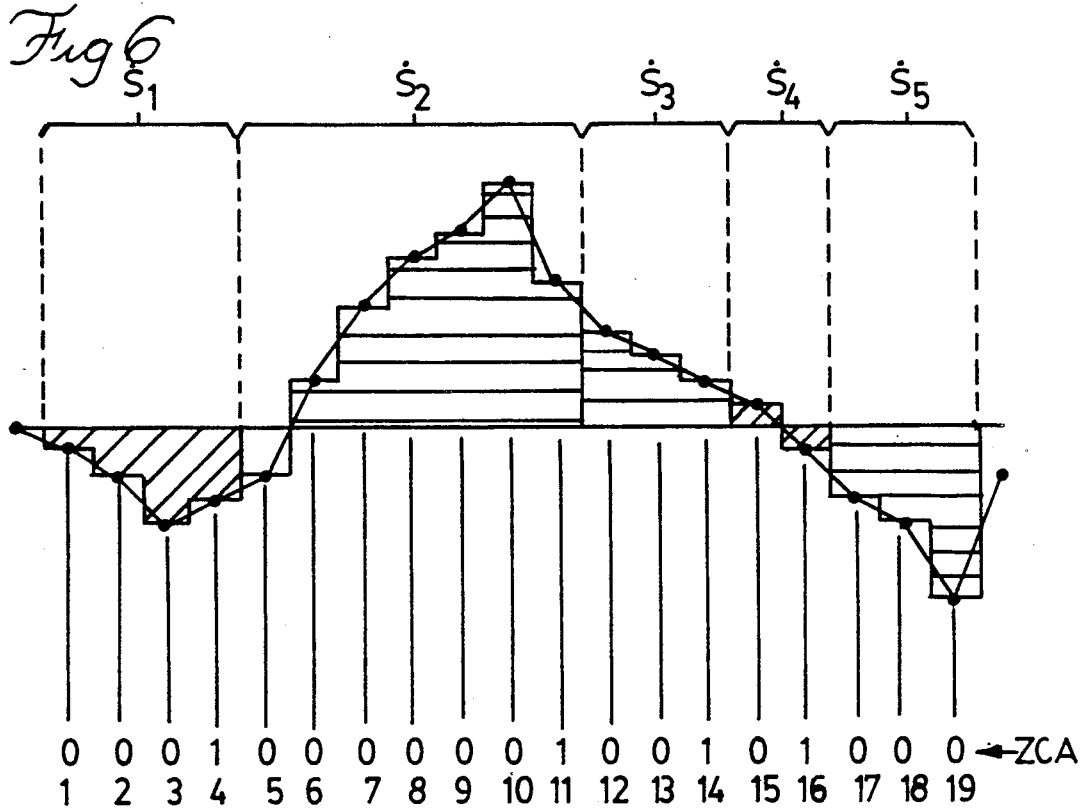
FIG. 6 is a graph of the derivative of a waveform which is partitioned by the Zero Crossing Array. (ZCA) for construction of the derivative areas $S_k$ for use in the method of the present invention.

Now, assuming the template points and signal points are numbered consecutively as shown in FIGS. 5 and 6 (below the ZCA), then we have, for this digital implementation:

for the template:

$T_1 = t_1 + \ldots + t_4$ $T_2 = t_5 + \ldots + t_{11}$ $T_3 = t_{12} + \ldots + t_{14}$ $T_4 = t_{15} + \ldots + t_{16}$ $T_5 = t_{17} + \ldots + t_{19}$ for the waveform under analysis $S_1 = s_1 + \ldots + s_4$ $$S_2 = s_5 + \ldots + s_{11}$$

$$S_3 = s_{12} + \ldots + s_{14}$$

$$S_4 = s_{15} + \ldots + s_{16}$$

$$S_5 = s_{17} + \ldots + s_{19}$$

Using the fundamental theorem of calculus for continuous time these can equivalently be written as:
for the template $$T_1 = t_4 - t_1$$

$$T_2 = t_{11} - t_5$$

$$T_3 = t_{14} - t_{12}$$

$$T_4 = t_{16} - t_{15}$$

$$T_5 = t_{19} - t_{17}$$

for the waveform under analysis $$S_1 = s_4 - s_1$$

$$S_2 = s_{11} - s_5$$

$$S_3 = s_{14} - s_{12}$$

$$S_4 = s_{16} - s_{15}$$

$$S_3 = s_{19} - s_{17}$$

In this way the first and second sets of identifiable partitions include linear data rather than area data as in the first embodiment.

While the best mode for practicing the invention has herein been described in detail, those skilled in the art to which this invention relates will recognize various alternative designs and embodiments for practicing the invention as defined by the following claims.

What is claimed is:

1. A method for monitoring an electrocardiographic signal and detecting a pathological cardiac arrhythmia, such as ventricular tachycardia from said signal in a subject such as a human, and providing a therapy signal therefore the method comprising the steps of:

(a) generating a reference template, the step of generating including the step of acquiring a first set of waveform data representing a known good electrocardiographic signal and processing the first set of waveform data to obtain the reference template and to separate the reference template into a first set of identifiable adjacent partitions having a boundary between said adjacent partitions, the step of processing including the step of determining the first derivative of the reference template, the first derivative being utilized to obtain boundary data representing the boundary;

(b) storing the first set of identifiable partitions and the boundary data;

(c) acquiring a second set of waveform data representing a 2-D waveform of an electrocardiographic signal being monitored;

(d) retrieving the first set of identifiable partitions and the boundary data;

(e) processing the second set of waveform data with the boundary data to separate the monitored waveform in to a second set of identifiable partitions;

(f) matching the first set of identifiable partitions with corresponding identifiable partitions of the second corresponding identifiable partitions of the second set to obtain a performance measure signal;

repeating steps (c), (e) and (f) until a plurality of electrocardiographic signals are analyzed and a corresponding plurality of performance measure signals have been obtained; and detecting a pathological cardiac arrhythmia based on the plurality of performance measure signals, providing a therapy signal in the event of said pathological cardiac arrhythmia.

2. The method as claimed in claim 1 wherein the first derivative is determined for a plurality of adjacent time intervals and wherein each boundary between adjacent partitions represents a change between a positive derivative and a negative derivative for the adjacent time intervals.

3. The method as claimed in claim 1 wherein the identifiable partitions of the first set of waveform data and the identifiable partitions of the second set of waveform data include area data.

4. The method as claimed in claim 1 wherein the identifiable partitions of the first set of waveform data and the identifiable partitions of the second set of waveform data include linear data.

5. The method as claimed in claim 1 further comprising the step of comparing the rate of the electrocardiographic signal being monitored with a predetermined rate.

6. A system for monitoring an electrocardiographic signal and detecting a pathological cardiac arrhythmia, such as ventricular tachycardia, from said signal in a subject, such as a human, and providing a therapy signal therefore the system comprising:

means for generating first and second sets of waveform data, the first set of waveform data representing a known good electrocardiographic signal, the first set of waveform data representing a 2-D reference waveform and the second set of waveform data representing a 2-D waveform of an electrocardiographic signal being monitored;

means for processing the first set of waveform data to separate the reference waveform into a first set of identifiable adjacent partitions having a boundary between said adjacent partitions, the means for processing including means for determining the first derivative of the reference waveform, the first derivative being utilized by said means for processing th obtain boundary data representing boundaries between adjacent partitions;

means for storing the first set of identifiable partitions and the boundary data;

means for retrieving the first set of identifiable partitions and the boundary data;

means for processing the second set of waveform data with the boundary data to separate the monitored waveform into a second set of identifiable partitions;

means for matching the first set of identifiable partitions with the corresponding set of identifiable partitions to obtain a performance measure signal; and means for detecting a pathological cardiac arrhythmia of the subject upon obtaining a plurality of performance measure signals, providing a therapy signal in the event of a pathological cardiac arrhythmia.

7. The system as claimed in claim 6 wherein the first derivative is determined for a plurality of adjacent time intervals and wherein each boundary between adjacent partitions represents a change between a positive derivative and a negative derivative for adjacent time intervals.

8. The system as claimed in claim 6 wherein the identifiable partitions of the first set of waveform data and the identifiable partitions of the second set of waveform data include area data.

9. The system as claimed in claim 6 wherein the identifiable partitions of the first set of data and the identifiable partitions of the second set of data include linear data.

10. The system as claimed in claim 6 further comprising means for comparing the rate of the electrocardiographic signal being monitored with a predetermined rate.

11. A method for monitoring an electrocardiographic signal and detecting a pathological cardiac arrhythmia, such as ventricular tachycardia from said signal in a subject such as a human, the method comprising the steps of:
(a) generating a reference template, the step of generating including the step of acquiring a first set of waveform data representing a known good electrocardiographic signal and processing the first set of waveform data to obtain the reference template and to separate the reference template into a first set of identifiable adjacent partitions having a boundary between said adjacent partitions, the step of processing including the step of determining the first derivative of the reference template, the first derivative being utilized to obtain boundary data representing the boundary;
(b) acquiring a second set of waveform data representing a 2-D waveform of an electrocardiographic signal being monitored;
(c) processing the second set of waveform data with the boundary data to separate the monitored waveform into a second set of identifiable partitions;
(d) matching the first set of identifiable partitions with corresponding identifiable partitions of the second corresponding identifiable partitions of the second set to obtain a performance measure signal; and repeating steps (b), (c) and (d) until a plurality of electrocardiographic signals are analyzed and a corresponding plurality of performance measure signals have been obtained and said pathological cardiac arrhythmia is detected.

12. A system for monitoring an electrocardiographic signal and detecting a pathological cardiac arrhythmia, such as ventricular tachycardia, in a subject, such as a human, the system comprising:
means for generating first and second sets of waveform data, the first set of waveform data representing a known good electrocardiographic signal, the first set of waveform data representing a 2-D reference waveform and the second set of waveform data representing a 2-D waveform of an electrocardiographic signal being monitored;
means for processing the first set of waveform data to separate the reference waveform into a first set of identifiable adjacent partitions having a boundary between said adjacent partitions, the means for processing including means for determining the first derivative of the reference waveform, the first derivative being utilized by said means for processing to obtain boundary data representing boundaries between adjacent partitions;
means for processing the second set of waveform data with the boundary data to separate the monitored waveform into a second set of identifiable partitions; and
means for matching the first set of identifiable partitions with the corresponding second set of identifiable partitions to obtain a performance measure signal and detect said pathological cardiac arrhythmia.

* * * * *